United States Patent [19]

Gwin

[11] Patent Number: 4,539,201
[45] Date of Patent: Sep. 3, 1985

[54] MEDICAMENT AND METHOD FOR INDUCING IMMUNITY TO INFECTIOUS BOVINE KERATOCONJUNCTIVITIS

[76] Inventor: Robert M. Gwin, 608 Stanton L. Young, Oklahoma City, Okla. 73104

[21] Appl. No.: 546,600

[22] Filed: Oct. 28, 1983

[51] Int. Cl.$^3$ .................. A61K 39/095; A61K 39/02; C12R 1/36; C12R 1/365
[52] U.S. Cl. ........................................ 424/92; 424/88; 424/93; 424/85; 435/871; 435/872
[58] Field of Search ........................ 424/88, 85, 92, 93, 424/177; 435/871, 872

[56] References Cited

U.S. PATENT DOCUMENTS 3,401,219  9/1968  Zeissiy .................................. 424/92

OTHER PUBLICATIONS

Wilcox, G E, *Aust. Vet. J.*, vol. 46, Jun. 1970, "Bacterial Flura of the Bovine Eye with Special Reference to the Moraxella and Neisseria".
Gurlay et al., *Ver. Record*, Apr. 19, 1964, pp. 416–417, "The Isolation of Large Colony and 7-Strain Micoplasmas from Cases of Bovine Keratoconjunctivitis".
*Stedman's Illustrated Medical Dictionary*, 24th Edition, published Williams & Wilkins, Baltimore 1982, p. 192.
Forsgren et al., *Chemical Abstracts*, vol. 91, 1979, No. 18217, "Many Bacterial Species Bind Igb".
Vacher et al., *Chemical Abstracts*, vol. 87, 1977, No. 28998b, "Immunostimulant Preparation".
Hours, M. et al., *Chemical Abstracts*, vol. 94, No. 145332k, "Antigens and Vaccines Containing Them".

*Primary Examiner*—Blondel Hazel
*Assistant Examiner*—Robin Lyn Teskin
*Attorney, Agent, or Firm*—Chris H. Morgan

[57] ABSTRACT

A medicament and method for inducing immunity in to infectious bovine keratoconjunctivitis in cattle. The medicament comprises the gram negative cocci Neisseria or Branhamella which are non-etiological agents of infectious Keratoconjunctivitis yet unexpectedly are found to afford an immunity to infectious bovine keratoconjunctivitis when administered to cattle.

11 Claims, 7 Drawing Figures

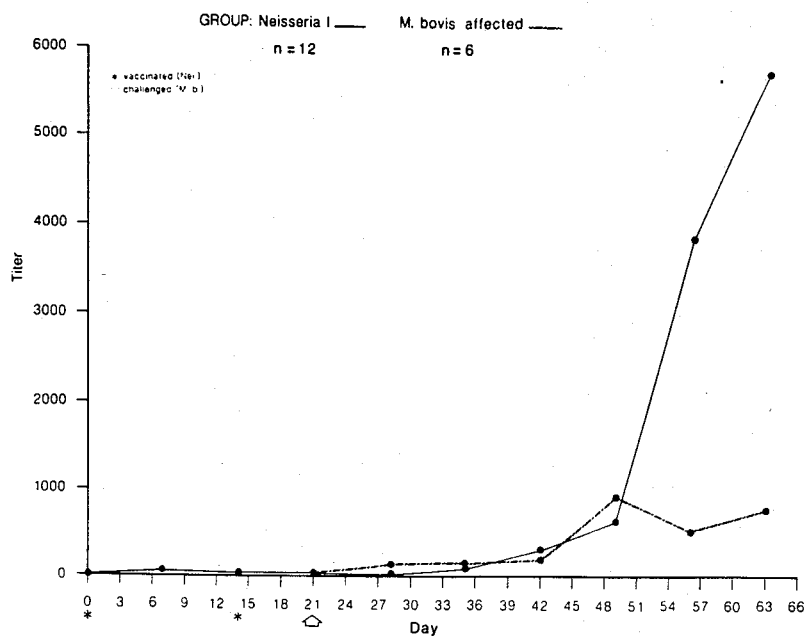
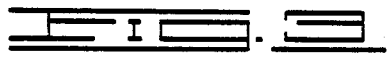
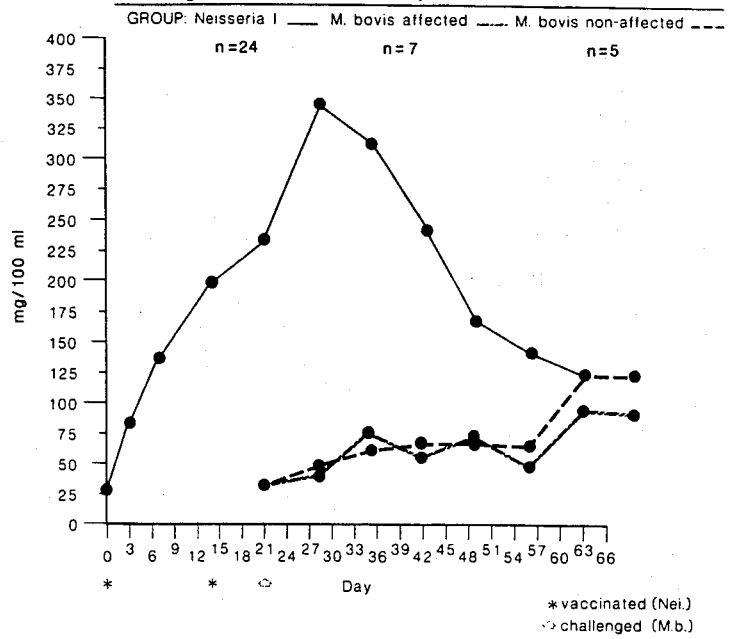
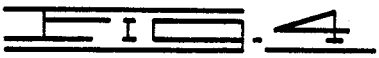

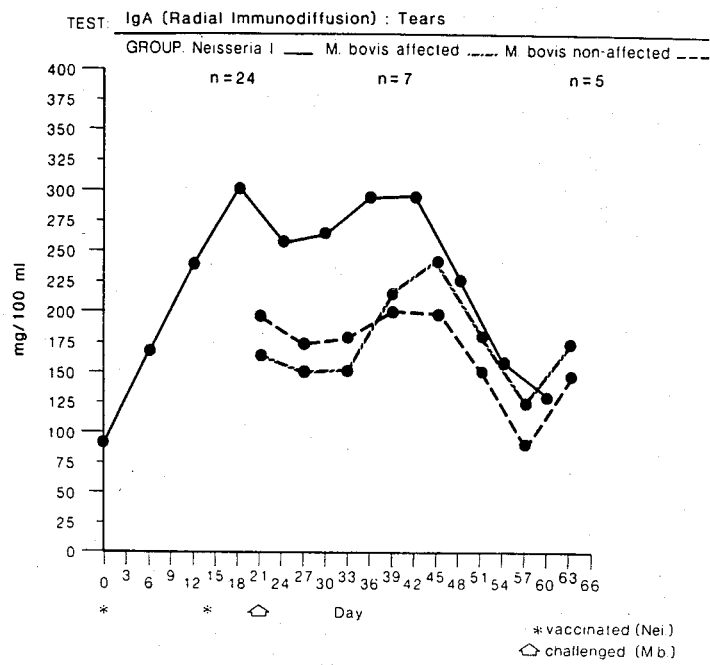
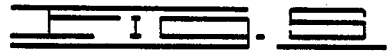
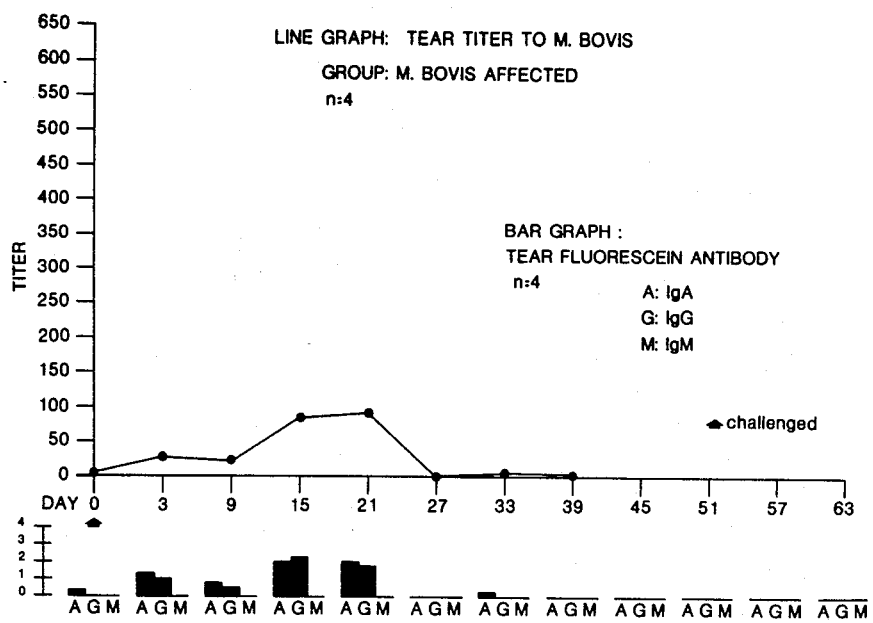
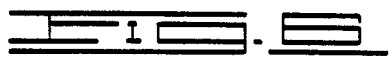

MEDICAMENT AND METHOD FOR INDUCING IMMUNITY TO INFECTIOUS BOVINE KERATOCONJUNCTIVITIS

BACKGROUND OF THE INVENTION

1. Field of the Invention

The present invention relates to prophylactic treatment and inducing immunity of infectious bovine keratoconjunctivitis which is a disease of the eyes of cattle commonly called Pinkeye caused by the bacteria *Moraxella bovis*. More particularly, the present invention relates to medicament or medicines and methods used in such treatment.

2. Description of the Prior Art

Pinkeye is a highly contagious disease of the eyes of cattle. The disease is characterized by an acute to chronic inflammation of the eye and impairs the sight of the animal. It affects cattle of all ages and breeds and is sufficiently debilitating to cause enormous financial loss in the cattle industry.

In the past, it has been discovered that pinkeye is caused by the bacteria *Moraxella bovis*. In an effort to provide prophylactic treatment for pinkeye, various viable and non-viable *Moraxella bovis* treatments have been prepared. It was thought that by means of varying the method of introduction or the method of attenuation of the *Moraxella bovis*, bacteria antibodies sufficient to provide immunity to pinkeye could be created in cattle. However, results from these efforts have not been entirely satisfactory. Apparently, introduction of *Moraxella bovis* does not create an immunity to itself in a manner which is either long lasting or effective for all cattle. Further, while infection in one eye of an animal may cause an immunity in that particular eye, the unaffected eye is not immunized and the same animal may be infected in the unaffected eye at a later time.

Treatment of diseased animals is somewhat impractical. It is difficult to administer medical treatment to a diseased animal in a range herd which is the most common location of the diseased animal. Moreover, methods of disease treatment which require special apparatus for immobilizing the animals head are difficult to utilize in the field. Curative results of treatment in an animal hospital are also not satisfactory. Accordingly, prophylactic treatment and immunization is the most practically beneficial method of treating pinkeye.

SUMMARY OF THE INVENTION

It is an object of the present invention to provide a medicament for inducing immunity to infectious bovine keratoconjunctivitis.

It is also an object of the present invention to provide an improved method of inducing immunity to infectious bovine keratoconjunctivitis.

In accordance with these objects, the present invention comprises a medicament for inducing immunity to infectious bovine keratoconjunctivitis. This medicament comprises an amount of gram-negative cocci selected from the genera of the family Neisseriaceae not including Moraxella effective to induce immunity to infectious keratoconjunctivitis. Preferably, the gram-negative cocci are selected from the genera Branhamella and Neisseria and do not include the species *Neisseria gonorrhoeae* and *Neisseria meningitidis*.

The method of the present invention comprises introducing in cattle an effective amount of the above described medicament so as to induce an immunity to infectious bovine keratoconjunctivitis. A particularly appropriate method of introducing the medicament comprises topical application of the gram-negative cocci in an appropriate carrier to an eye to be immunized.

Antibodies induced by the pinkeye disease or naturally occurring quantities of genera of the family Neisseriaceae do not provide immunity to pinkeye infection of previously undiseased eyes. By the medicament of the present invention and the method of treatment of the present invention, it has been discovered that bacteria other than the *Moraxella bovis* bacteria which causes pinkeye can produce antibodies sufficient to immunize against *Moraxella bovis* and, therefore, against infectious bovine keratoconjunctivitis. The medicament and treatment of the present invention do not cause any disease in the treated cattle.

For a further understanding of the invention and further objects, features and advantages thereof, reference may not be had to the following description taken in conjunction with the accompanying drawings.

BRIEF DESCRIPTION OF THE DRAWINGS

FIG. 3 is a graph illustrating bacterial agglutination titer to *M. bovis* (serum) test results related to the present invention;

FIG. 4 is a graph illustrating test results of a test for IgG in tears related to the present invention;

FIG. 5 is a graph illustrating test results of a test for IgA in tears related to the present invention;

FIG. 6 is a graph illustrating test results of *M. bovis* affected cattle related to the present invention.

DESCRIPTION OF THE PREFERRED EMBODIMENTS

Figure 1:
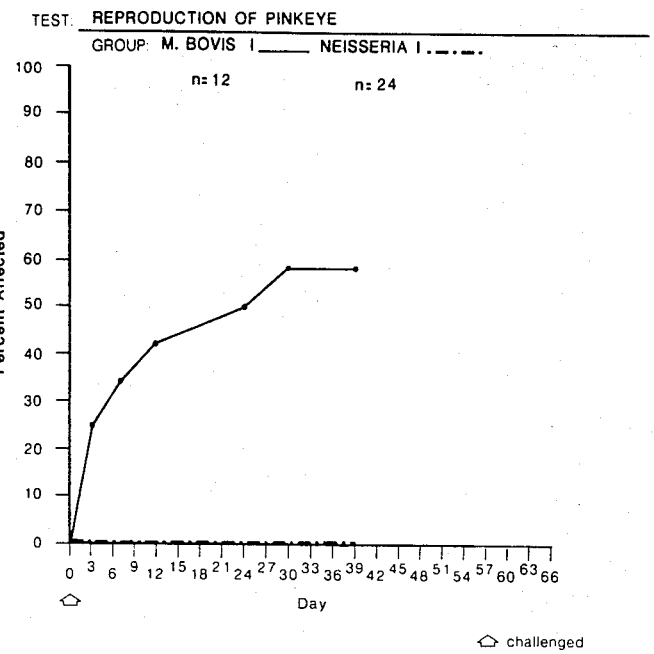
FIG. 1 is a graph illustrating reproduction of pinkeye test results related to the present invention.
Figure 2:
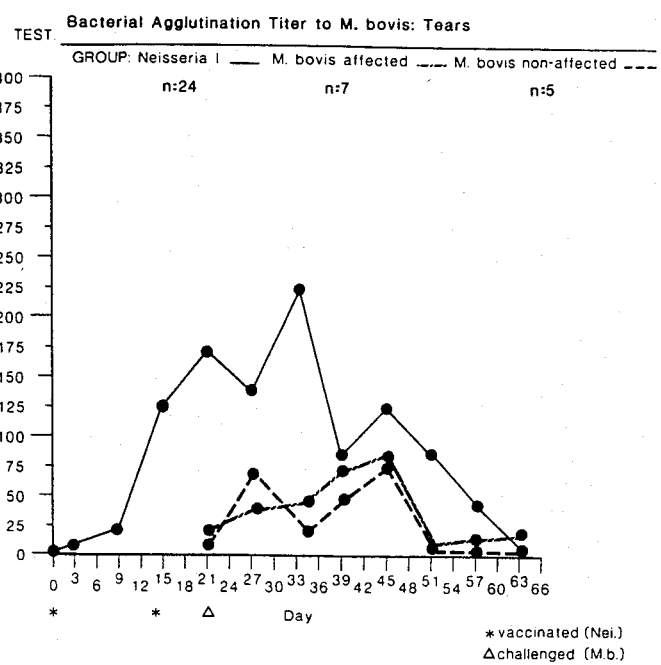
FIG. 2 is a graph illustrating bacterial agglutination titer to *M. bovis* (tears) test results related to the present invention.

As shown in the examples and tests set forth below, *Moraxella bovis* does not appear to be an effective immune stimulator. By the present invention, it has been discovered that gram-negative cocci of genera selected from the family Neisseriaceae not including Moraxella are effective immune stimulators and antibodies produced in this immune stimulation are effective to produce an immunity against the infectious bovine keratoconjunctivitis produced by *Moraxella bovis*.

It is not yet certain whether the most effective immune response is created by cocci selected from the genus Branhamella or the genus Neisseria. It is not thought that an appropriate medicament would include the species *Neisseria gonorrhoeae* and *Neisseria meningitidis* in that these species are extremely dangerous to humans.

*Moraxella bovis* is considered to be the main causative agent of infectious bovine kertoconjunctivitis (IBK), commonly known as pinkeye. IBK has been reproduced with *M. bovis* organisms alone and in combination with other enhancing factors.

Numerous attempts have been made to produce a pinkeye vaccine utilizing viable and nonviable *M. bovis* organisms in both experimental and natural environmental conditions. In most cases these vaccines consisted of a heat-killed, formalin-killed, or viable autogenous M. bovis bacteria injected at weekly intervals intramuscularly or into the third eyelid. While in many cases M. bovis antibodies were produced, fewer positive cultures were obtained, and the severity of lesions were frequently reduced, vaccinations did not produce practical protection against the disease. Other factors such as age, vaccination schedule, and the use of homologous stains of *M. bovis* have been studied.

*M. bovis* may exist in either a smooth or rough colony form, with rough colonies exhibiting pili extending from the cell walls. These pili are delicate elongated unbranched filaments which contain no central pore and have a peritricous distribution. Pili appear to provide additional extracellular antigens, which may be of importance in development of resistance to the organism. Studies by others using an *M. bovis* pilus vaccine have indicated a stimulation of immune response to *M. bovis* which may provide a more protective immunity than previous *M. bovis* vaccines. However, such a vaccine is not as desirable as the vaccine of the present invention which does not utilize *M. bovis* in any viable, non-viable or attenuated form.

Local resistance to bacterial infection of corneal and conjunctival surfaces is a complex system involving several antibacterial substances, including secretory IgA, lysozyme, beta-lysin, and lactoferrin. *M. bovis* antibodies have been found in cattle tears and, while increased during active infection, resistance is not necessarily associated with high antibody levels.

In tests described below, IBK was reproduced in calves in 66% of innoculated eyes using virulent *M. bovis* organisms alone. The tests did not reveal demonstrable alterations in tear or serum levels of IgA, IgG or IgM. Tear antibodies were produced in both affected and non-affected calves, but did not appear to provide any protection from the disease. Lysozyme, a potent antibacterial agent in human tears, was not found in any calves.

The purpose of the tests set forth was to examine the clinical and immunological responses of calves administered a non-virulent bacterial vaccine prior to challenge with a virulent *M. bovis and to compare these results to those obtained from non-vaccinated calves challenged with the same organism.*

MATERIALS AND METHODS FOR TESTS

Subjects: Twelve week old Holstein calves, free from any clinical disease or infection, were used. Prior to use, a thorough examination of the anterior segment was performed. All calves were kept inside a building in a fly-free environment with no exposure to sunlight.

Test Group: Calves were divided into two groups:

1. Control Group: Six calves (12 eyes) were used as positive controls and received virulent *M. bovis* in an effort to produce disease.
2. Vaccinated Group: Twelves calves (24 eyes) were vaccinated with a live non-attenuated bacteria on day 0 and revaccinated on day 14. On day 21 these calves were challenged with the virulent *M. bovis* in a manner identical to the control group.

Collection of Tears: Tear samples were collected with nonheparinized capillary tubes placed in the lower cul-de-sac of the eye following physical restraint with a halter and ropes. Approximately 0.5 ml of tears was collected from each eye and placed in the micro-centrifuge vials and stored at −40° C.

Determination of disease: All animals were examined daily for the presence of significant eye diseases, synptoms of which included blepharospasms, increased lacrimation, conjunctivitis, corneal opacification, ulceration and rupture. Affected eyes were sequentially photographed on a weekly basis.

*M. bovis* and Neisseria-Branhamella Vaccine Antibody

Production: Four healty New Zealand white rabbits, weighing 8–10 pounds, were used for antibody production against the *M. bovis* and Neisseria-Branhamella vaccine organisms (2 rabbits each). Each rabbit received six separate subcutaneous injections of 0.5 ml of live bacterial in trypticase soy broth (TSB) ($8\times10^6$ organisms/ml). The injections were repeated in five days and blood was taken two weeks after the second injections, and then at two week intervals. Blood samples were centrifuged for ten minutes and the serum removed and frozen at −40° C.

Bacterial Vaccine Production and Inoculation: A Neisseria-Branhamella bacteria was isolated and grown on 5% BBA for 48 hours at 37° C. using standard isolation and growth techniques. Bacterial growth was scraped from plates and suspended in TSB to a concentration of $5\times10^6$ organisms/ml as determined from BBA plate counts and chamber count. This suspension of live bacteria was the vaccine, and was applied topically to the eye (0.5 ml/eye) on days 0 and 14 in 12 calves (24 eyes).

The Neisseria-Branhamella bacteria was tested in separate tests to determine that the bacteria was of the genus Neisseria or the genus Branhamella or both. Results of these tests are set forth in Table I and Table II below.

TABLE I

Characteristics of Neisseria-Branhamella used for the Pinkeye Study

| | | | | | |
|---|---|---|---|---|---|
| 1. | Gram − diplococcus | | | | |
| | Oxidase + | | | | |
| | Catalase + | | | | |
| 2. | Fermentation: | | | | |
| | Glucose | Maltose | Lactose | Sucrose | Fructose |
| | 0 | 0 | 0 | 0 | 0 |
| | NO₃ Reduction | | | Deoxyribonuclease | |
| | 0 | | | 0 | |
| 3. | Growth on Nutrient Agar | | Growth on Brain Heart Infusion Agar | | |
| | 28° C. | 37° C. | 28° C. | | 37° C. |
| | + | + | + | | + |
| | Growth on 5% Bovine Blood Agar Plate | | | | |
| | 37° C. | | | | |
| | + | | | | |

0 = No Fermentation
+ = Positive or presence of Growth.

TABLE II

| Neisseria - Branhamella |
|---|
| 1. Gram-negative cocci .6–.9μ in diameter |
| 2. In pairs with adjacent sides flattened |
| 3. Oxidase positive |
| 4. Catalase positive |
| 5. Non-mobile |
| 6. Grows at 25° C. on trypticase-soy agar without blood-aerobic |
| 7. Nitrate reduction negative |
| 8. Carbohydrate utilization (C + S): No acid from glucose, lactose, maltose, sucrose, xylose, fructose, mannitol, and arabinos |
| 9. Urease negative |
| 10. Phenylalanine negative |

TABLE II-continued

Neisseria - Branhamella

11. Citrate utilization negative
12. H$_2$S negative
13. Arginine dehydrolase negative
14. Ornithine decarboxylase negative
15. Lysine decarboxylase negative
16. Indole negative
17. V-P negative
18. Gelatin liquefied Challenge with Virulent *M. bovis:* Both the positive control group (challenge only) and the vaccinated group were challenged in an identical fashion with the same *M. bovis* organism. A virulent hemolytic *M. bovis* was grown on 5% BBA for 48 hours, removed from the plates and suspended in TSB with a concentration of $8 \times 10^6$ organisms/ml. This inoculum was applied directly to the eye in one/half of all the calves.

Calves not challenged with the TSB inoculum were challenged with a pure bacterial paste. In these calves, the virulent *M. bovis* was grown for 48 hours on BBA. The bacterial growth from one plate was then removed and applied directly to the eye.

The vaccinated group was challenged on day 21, one week following the second vaccination.

Determination of Tear and Serum Antibody Titers to *M. bovis* and Neisseria-Branhamella by Bacterial Agglutination: Lyophilized samples of *M. bovis* and Neisseria Branhamella were reconstituted with 0.3 ml TSB and streaked on three 5% BBA plates. Bacterial organisms (0.5 ml) were removed after 48 hours and suspended in 5 ml phosphate buffer solution (PBS) at a pH of 7.2. This suspension was washed three times with PBS. One ml of this bacterial stock solution was diluted with 3 ml of PBS for a 1:4 dilution.

Ten microliters of PBS was placed in each well of a Falcon plate. Ten microliters of the sample to be tested was then placed in the first well and a serial twofold dilution was performed. Following this, 10 microliters of either the diluted *M. bovis* and Neisseria-Branhamella bacterial stock solution was placed in all wells. After 24 hours the plates were read for positive agglutination of bacteria.

Determination of Anti-*M. bovis* Immunoglobulins in Tears: The positive bacterial agglutination reactions for four affected controls and four vaccinated calves were collected and washed three times with PBS and the bacteria removed. The bacteria were divided into three separate tubes, to which fluorescein conjugated anti-bovine IgA, IgG and IgM were added. Following one hour incubation at room temperature, the bacteria were washed three times in PBS, placed on a slide and examined for fluorescence with an Olympus U-V microscope. The reaction was graded on a scale of 0 to +4, depending on the degree of fluorescence by two independent examiners. In cases of discrepancy, the lower of the two values was used.

Determination of General Immunoglobulin Levels in Tears: A single radial immunodiffusion method was employed for the quantitative determination of tear immunoglobulins IgA, IgM and IgG. Tear samples and control standards were placed in wells and incubated at room temperature for 24 hours. After incubation, zones of precipitation were measured and the concentration determined from a standard curve.

Terminology:

The word infected is defined as "to contaminate with a disease-producing substance or agent". All calves were infected with *Moraxella bovis.* The control calves were infected (challenged) at day 0, while the vaccinated group was infected (challenged) at day 21 following two vaccinations with Neisseria-Branhamella at day 0 and day 14.

In the FIGS. the single genus "Neisseria" is used with respect to the Neisseria-Branhamella vaccine produced and tested in the Table I and Table II tests set forth above.

RESULTS OF TESTS

Reproduction of IBK

Positive Controls: Six calves (12 eyes) were directly inoculated with 0.5 ml virulent *M. bovis* organisms. While all six calves developed pinkeye, 58% (7 eyes) of the total number of eyes developed significant disease (FIG. 1). The onset of disease was rapid, with most calves developing significant pinkeye by day 12. The lesions appeared identical to the natural disease with progressive corneal ulceration, etc. Both the bacterial paste and TSB suspension were capable of producing disease, with the paste producing a more acute and severe process than the TSB suspension.

Neisseria-Branhamella Vaccine Group: Twelve calves (24 eyes) were challenged with virulent *M. bovis* organisms in a manner identical to the positive controls, following Neisseria-Branhamella vaccination. None of the calves developed any sign of IBK for the 42 days of post challenge observation.

Bacterial Agglutination Titers to *M. bovis*

Tears: In the positive control group, both affected and non-affected eyes developed a similar antibody response which rose to a high of approximately 1:75 at three weeks post challenge, then dropped off precipitously (FIG. 2).

In the vaccinated group, the titers to *M. bovis* rose above 1:150 before the challenge (day 21) and peaked at over 1:200 by day 33 (FIG. 2). As in the positive control group, the titer then dropped off quickly.

Serum: Titers in both the challenge and control groups remained low for the first three weeks post challenge (FIG. 3). At that time an increasing titer was observed in both groups. In the control calves the titer leveled off after reaching a high of slightly over 1:900. The vaccinated calves developed a tremendous rise in titer to *M. bovis,* which was nearly 1:600 in the final sample studied.

Tear Immunoglobins

Three classes of immunoglobulins were studied (IgA, IgG and IgM). Tear IgM levels were consistently too low to measure and are not included.

Low levels of IgG were present in baseline tears of both groups (FIG. 4). In control calves a slow three-to-five fold increase in tear IgG was observed post challenge with little variation between affected and non-affected eyes. In the vaccinated group, however, tear values were near 1:225 at the time of challenge. This titer peaked seven days following challenge at over 1:325 and then dropped off rapidly. This represented a thirteenfold increase in IgG.

Baseline levels of tear IgA were higher in the control calves than the vaccinated group (FIG. 5). In the control group, both affected and non-affected eyes demonstrated a slight rise in tear IgA two weeks following challenge, which then fell to below base-line levels.

In vaccinated calves, tear IgA levels increased threefold during the vaccination phase, demonstrated a leveling off phase for three weeks post challenge, then dropped off rapidly.

Classification of Anti-*M. bovis* Antibodies

Positive Controls: In tear samples collected from four affected control calves, antibodies from both the IgA and IgG classes were present, peaking out between two and three weeks post challenge, after which they were essentially non-detectable (FIG. 6). This was comparable to the mild tear titer response seen in the same four calves at days 15 and 21 (FIG. 6).

Figure 7:
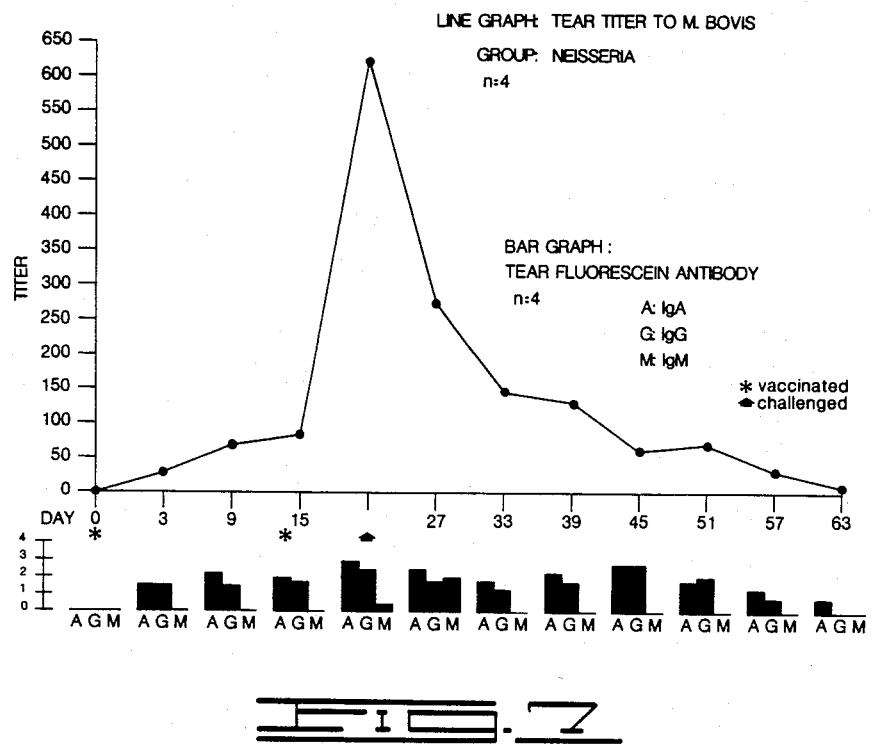
FIG. 7 is a graph illustrating test results of Neisseria-Branhamella vaccinated cattle related to the present invention.

Neisseria-Branhamella Vaccine Group: In the four vaccinated calves studied, a greater and more sustained response was seen. By day 21, just prior to challenge, tear titers slightly over 1:600 were associated with high levels of IgA and IgG bound to the bacteria (FIG. 7). Following the challenge there was a marked drop in tear titers, although the fluorescent antibody test demonstrated continued high levels for over three weeks post challenge.

DISCUSSION

The above tests show it is readily possible to reproduce clinical IBK with the use of virulent *M. bovis* organisms alone. The disease was indistinguishable from the naturally occurring disease in clinical development and progression. The Neisseria-Branhamella vaccine provided complete protection under the controlled environment of this study.

*M. bovis* does not appear to be an effective immune stimulator. The slight rise in tear antibodies was transient and minimal. The lack of antibody variation in affected and non-affected calf tears suggests the absence of any meaningful protection against the disease. The minor immune response was associated with IgA and IgG antibody production, however, these were virtually nondetectable after three weeks post challenge, and were associated with slight changes in gross IgA and IgG tear levels.

The Neisseria-Branhamella vaccine was in comparison a far superior stimulator of the immune system against *M. bovis* antigens. Prior to challenge, the vaccine stimulated a marked increase in tear *M. bovis* antibodies, which was concomitant to increasing levels of tear IgA and IgG. These levels were substantially greater than the control group in either affected or non-affected calves throughout the test period.

Fluorescein antibody studies confirmed that the increased levels of IgA and IgG in tears were, in fact, associated with *M. bovis* antibody production. While no antibody was detected on day 0, significant levels were already detectable three days following initial vaccination. At the time of challenge with *M. bovis*, these values were much higher than at any time in affected control calves, and remained high for over three weeks post challenge. In control affected calves, prominent fluorescein antibody tagging of bacteria was found on days 15 and 21 post challenge, after which they were essentially absent.

Other studies have indicated several cross antigens between the Neisseria-Branhamella vaccine and *M. bovis*. This apparent cross antigenicity appears to be the basis for the induced protective immunity to *M. bovis*. This is especially significant since *M. bovis* does not produce similar immunity to itself. This lack of auto-immunity may be the key to both the pathogenicity of *M. bovis* in bovine cornea and the difficulty of previous investigators in using *M. bovis* in various forms as an effective vaccine against itself. On the basis of the above test results, it is indicated that gram-negative cocci of genera in the family Neisseriaceae other than Moraxella are an effective medicament to induce immunity in cattle to pinkeye. Bacterial agglutination tests of various Neisseria-Branhamella bacteria similar to the bacteria in Tables I and II show variable degrees of ability to produce antibody against *M. bovis*. The results in Tables I and II were for the bacteria most effective in producing antibodies against *M. bovis*.

It is thought that viable, non-viable and attenuated forms of the genera of the family Neisseriaceae other than Moraxella would be effective for producing immunity. However, viable forms would be most effective and do not produce any disease in the cattle.

The preferred medicament comprises gram-negative cocci selected from the genera Neisseria and Branhamella. It is also preferred not to use the species *Neisseria gonorrhoeae* and *Neisseria meningitidis* since these species are extremely dangerous to humans. It may be preferred to use a single selected species or only species selected from a single one of the genera Neisseria and Branhamella.

Various methods of introducing the medicament to cattle are thought to be effective to produce immunity to pinkeye. For example, intramuscular injections or ocular injections are thought to be effective. Oral introduction and other methods of introduction may also be effective. Topical application to the eye as set forth in the tests is preferred.

Thus, the medicament and method of treatment are well suited to achieve the objects and advantages described as well as those inherent therein. While presently preferred embodiments of the invention have been described for the purpose of this disclosure, various changes can be made by those skilled in the art which changes are encompassed within the spirit of this invention is defined by the appended claims.

The foregoing disclosure and the showings in the examples and drawings are merely illustrative of the principles of this invention and are not to be interpreted in a limiting sense.

What is claimed is:

1. A medicament which induces immunity to infectious bovine Keratoconjunctivitis when administered to cattle comprising: an amount of gram-negative cocci selected form the group consisting of the genera Neisseria and Branhamella in combination with a pharmaceutically acceptable carrier wherein the amount introduced is effective to induce immunity to infectious bovine Keratoconjunctivitis when administered to said cattle.

2. The medicament of claim 1 wherein said gram-negative cocci are selected from the genus Neisseria.

3. The medicament of claim 2 wherein said cocci from the genus Neisseria are selected from species which are non-pathogenic in cattle.

4. The medicament of claim 1 wherein said gram-negative cocci are selected from species of the genera Branhamella and Neisseria which are non-pathogenic in cattle.

5. The medicament of claim 1 wherein said gram-negative cocci are selected from the genus Branhamella.

6. The medicament of claim 1 wherein said pharmaceutical carrier is suitable for topical application to the eye.

7. A method of inducing immunity to infectious bovine keratoconjunctivitis in cattle comprising:
   introducing in cattle an amount of gram-negative cocci selected from the Neisseria and Branhamella in combination with a pharmaceutically acceptable carrier; wherein said amount is sufficient to induce immunity to infectious bovine keratoconjunctivitis in said cattle.

8. The method of claim 7 wherein said gram-negative cocci are of the genus Branhamella.

9. The method of claim 7 wherein said gram-negative cocci are of the genus Neisseria.

10. The method of claim 9 wherein said gram-negative cocci are selected from species of the genus Neisseria which are non-pathogenic in cattle.

11. The method of claim 7 wherein said introducing is by topical application to the eyes of cattle to be immunized.

* * * * *